United States Patent [19]

Myerholtz et al.

[11] 4,333,336
[45] Jun. 8, 1982

[54] APPARATUS FOR COMPUTING FLOW RATE OF THERMOPLASTIC MATERIAL

[75] Inventors: Carl A. Myerholtz; Ralph W. Myerholtz, Jr., both of Naperville, Ill.

[73] Assignee: Standard Oil Company (Indiana), Chicago, Ill.

[21] Appl. No.: 148,153

[22] Filed: May 7, 1980

[51] Int. Cl.³ ............................................. G01N 11/04
[52] U.S. Cl. ....................................................... 73/56
[58] Field of Search ...................... 73/56, 55, 54, 15.4

[56] References Cited

U.S. PATENT DOCUMENTS

| | | | |
|---|---|---|---|
| 3,807,221 | 4/1974 | Brown et al. | 73/57 |
| 4,062,225 | 12/1977 | Murphy, Jr. et al. | 73/60 |
| 4,109,516 | 8/1978 | Fuxa | 73/93 |
| 4,241,602 | 12/1980 | Han et al. | 73/56 |

OTHER PUBLICATIONS

ASTM Standard No. D 1238-79, pp. 468-479, 1979.
Advertisement for Monsanto "Automatic Capillary Rheometer", 3 pages, No date.
Advertisement for Melt Rheometer in Apr., 1980, issue of "Laboratory Equipment", vol. 16, No. 12.

Primary Examiner—Jerry W. Myracle
Attorney, Agent, or Firm—Ronald C. Petri; William T. McClain; William H. Magidson

[57] ABSTRACT

Disclosed is a method and device for automatically and instantaneously computing and displaying with high precision the flow rate of thermoplastic samples run in an extrusion plastometer in accordance with American Society of Testing Materials (ASTM) Method D1238. The method and device comprise using a microcomputer and related circuitry to monitor and control the measurement process and subsequently compute the resulting flow rate.

7 Claims, 3 Drawing Figures

MIK CONTROLLER SCHEMATIC DIAGRAM

APPARATUS FOR COMPUTING FLOW RATE OF THERMOPLASTIC MATERIAL

BACKGROUND

This invention relates to a novel device and method for determining the flow rate of thermoplastic materials. In particular, this invention relates to a device and method for determining flow rate which utilizes electronic circuitry to monitor the extrusion or displacement of a known volume of a thermoplastic sample and conveniently calculate the flow rate of said sample. More particularly, this invention relates to a novel device and method which automatically and instantaneously computes and displays with high precision the flow rate of thermoplastic samples run in an extrusion plastometer in accordance with American Society of Testing and Materials (ASTM) Method D1238. This invention also relates to other types of melt, liquid, or solution viscosity measurements in which a flow or efflux time is measured and for which a simple computational constant can be derived.

The melt flow rate or "melt index" of thermoplastics as determined by ASTM Method D1238 (Current edition approved Jan. 26, 1979; published February, 1979; originally published as D1238-65T; last previous edition D1238-73—hereby expressly incorporated herein by reference), or foreign counterparts, is universally employed as a specification or inspection property. As a result, the extrusion plastometer is widely used in polymer manufacturing plants, polymer fabrication plants, technical service, research and other laboratory installations the world over. More recently, a variety of plastometer configurations have been developed. Examples of such plastometers are Brown et al. (U.S. Pat. No. 3,807,221), Murphy et al. (U.S. Pat. No. 4,062,225) and Fuxa (U.S. Pat. No. 4,109,516).

In Procedure A of ASTM Method D1238, the operator manually cuts off portions of extrudates at specified time intervals and weighs them on a balance accurate to ±0.001 g. This procedure is time consuming, requires an expensive balance as an accessory, and is subject to errors in both collecting extrudates at exact time intervals and in the weighing step. The final result is calculated manually in accordance with the test method. Procedure B of ASTM Method D1238 involves the use of an automatically operated timer to determine the time required to extrude a known volume of polymer. The flow rate is then determined from the following relationship Flow rate = F/t where F is a numerical factor which takes into account the volume extruded, the size of the piston used to extrude or displace the polymer, and the density of the polymer melt; and t is the time taken to extrude the known volume. Values of F are different for each polymer and are well known in the art. The method still involves a manual calculation of the result and is subject to the potential incorrect entry of the numerical factor each time the calculation is repeated. Precision may also be limited by the type of timing device used. Our invention overcomes the limitations of the currently-used procedures mentioned above through the use of a low cost microprocessor and supporting circuitry.

Previous attempts at an automatic flow rate measuring and method, most notably the Monsanto Automatic Capillary Rheometer, remain limited by the fact that the actual computation of flow rate must be performed each time by the user. In addition, such "automatic" devices are basically little more than sophisticated timers—the user is still required to read the timers and perform the subsequent calculations.

In contrast, the device and method of this invention requires only that the user input the numerical factor characteristic of the particular material being measured. All timing and control functions of the measurement, as well as all computational functions, are subsequently directed by a microprocessor and supporting circuitry. The flow rate is then displayed by means of the output device of choice.

The apparatus of this invention utilizes Procedure B of ASTM Method D1238. In accord with this method, the material to be measured is first preheated for a short period to prepare it for extrusion. A weighted piston of known surface area is then used to force material through a barrel and extrusion plastometer orifice of known dimensions. The measurement is based upon determining the time required to displace a known volume of material.

SUMMARY OF THE INVENTION

This invention is an improvement in the established methods of determining physical characteristics of thermoplastic materials. More specifically, in a method for determining the flow rate of a thermoplastic material in accord with Procedure B of ASTM Method D1238 using an extrusion plastometer, the improvement of the present invention comprises entering one or more numerical factor specified by said ASTM Method D1238 for said thermoplastic material into an input/output device capable of being read by a microprocessor, using one or more programmed microprocessors to (a) initiate an electronically timed interval when a change of state is detected in a switch designed to undergo a first change of state after displacement of said thermoplastic material begins in said plastometer; (b) check the status of said switch at predetermined intervals; (c) end said electronically timed interval when said switch undergoes a second change of state upon the displacement of a predetermined volume of said thermoplastic material; (d) determine the duration of said timed interval; and (e) calculate the flow rate for said thermoplastic material by dividing said factor by the duration of said timed interval, and displaying said flow rate in a convenient input/output device.

In addition, the present invention also provides an improved device for determining physical characteristics of thermoplastic materials. More specifically, in a device for determining the flow rate of a thermoplastic material in accord with Procedure B of ASTM Method D1238 using an extrusion plastometer, the improvement of the present invention comprises means for entering one or more numerical factors specified by said ASTM Method D1238 for said thermoplastic material into an input/output device capable of being read by a microprocessor; means for initiating an electronically timed interval when a change of state is detected in a switch designed to undergo a first change of state after displacement of said thermoplastic material begins in said plastometer; means for checking the status of said switch at predetermined intervals; means for ending said electronically timed interval when said switch undergoes a second change of state upon the displacement of a predetermined volume of said thermoplastic material; means for determining the duration of said timed interval; means for calculating the flow rate for said thermoplastic material by dividing said factor by the duration of said timed interval; and means for displaying said flow rate in a convenient input/output device.

Any means of starting and stopping the timing operation may be used. A readily available mechanical switch ("timer actuating switch") is described in detail as part of ASTM Method D1238. This switch is normally closed and is connected to a split-second timer. At some point after the extrusion begins, the switch changes state (opens) and the timer is started. The switch changes state again, (closes), and stops the timer, after a cylinder of the polymer of known length and diameter (and therefore, volume) is extruded or displaced. The operator then performs the flow rate calculation after reading the timer and looking up the appropriate numerical factor F for the material.

In accord with the method of this invention, a similar mechanical switch can be used. However, other sensing devices such as microswitches, light beam-photocell units, capacitance or inductance operated switches, and the like, can also be used. A normally open switch can also be used with suitable electronic or program modifications obvious to those skilled in the art. The switch signal is connected to the peripheral interface adapter (PIA) board.

In accord with our invention, the numerical factor pertaining to the material to be measured is input into the microprocessor by means of a convenient input/input device. Such devices can include thumbwheel switches, a keyboard, or magnetic tape—the choice in most cases being determined by the sophistication of the microprocessor and the expense of the additional peripheral equipment.

In one aspect, a set of four indicating binary coded decimal (BDC) thumbwheel switches function to enter the numerical factor used in the computation. Once set, no further manipulation of these switches is required unless the factor is to be changed to run a different type of polymer. These thumbwheel switches are connected to the PIA board through type 74153, or equivalent, multiplex chips to allow each switch's status to be read individually, because there are insufficient inputs to handle all switch leads simultaneously.

In one embodiment, the computational program can be stored on magnetic tape and then loaded in the 1K of random access memory (RAM) on the microcomputer board. In this aspect, the program need not be loaded again, except in case of a power failure, causing loss of the data in RAM. Alternatively, in the preferred embodiment the program can be permanently stored in a separate read only memory (ROM) chip which will be interfaced with suitable circuitry. In this aspect, the program can be permanently stored and there will be no need to load from magnetic tape, even in the event of power failure.

Once the extrusion interval has been timed as the interval between the two changes in state of the sensing switch, the factor is read by the microprocessor and the computation is performed. The result of the computation, the flow rate, is then displayed by means of a convenient input/output (I/O) device, such as an LED display or a printer.

A "reset" button is provided which consists of a momentary contact switch connected to the central processing unit (CPU) chip of the microprocessor, and functions to clear the previous computation in preparation for the next run.

The principal features of operation in accord with the preferred embodiment of the present invention are:
1. Pressing the reset button clears the result of the previous measurement, and prepares the timer and circuitry for the next measurement.
2. The run is begun by applying the required load to the piston of the extrusion plastometer, thereby starting the extrusion.
3. When the sensing switch changes state at the start of the measuring interval, an interrupt routine is initiated which checks the status of the switch at predetermined intervals.
4. A "debounce" routine is included to ignore any subsequent changes of state of the sensing switch for a suitable interval of 0.1 to 0.5 second. This tends to eliminate sensitivity to vibration and avoids false shutoff of the timing function caused by bouncing of the switch contacts.
5. When the measurement interval is complete and the sensing switch again changes state, the settings of the thumbwheel switches are read. The flow rate is calculated through the relationship Flow rate = $F/t$ where F is the factor entered via the thumbwheel switches and t is the time measured.
6. The result is then displayed.

The worker skilled in the art will note that refinements are readily apparent. One such improvement would be to incorporate a means of signalling the end of a 5 minute "preheat" period as a convenience. In this embodiment, two displays would be in use: one to indicate the flow rate result, and the other to indicate the elapsed (preheat) time since the reset button was pressed. Such a display of the elapsed time after reset would serve to time the preheat period and signal the end of the preheat period and the start of the measurement run. This feature can be provided through a second interrupt program and can derive its time base from a crystal controlled oscillator on the microprocessor circuit board. Both this display and the one used to display the result can be multiplexed by the microprocessor to reduce the number of electronic components needed. The incorporation of a printer to provide a "hard copy" of the result on the display is also contemplated as well as provision to allow operation of several extrusion plastometers with one microcomputer unit, if desired.

The advantages of this apparatus also are readily apparent. It provides more precise results and eliminates several possible sources of operator error, eliminates the time required for manual computation and eliminates the need for a balance. With this instrument, a single technician can operate several extrusion plastometers simultaneously since it is not necessary for him to collect and weigh extrudates, or operate a timer or perform calculations. This would be of particular advantage in manufacturing installations. Its simplicity and low cost will allow it to be used with existing extrusion plastometers without modification.

This same apparatus can be adapted to many other types of viscosity measurements in which a flow time is measured and for which a suitable constant can be developed. Examples include measuring the viscosity of motor oils and other petroleum or synthetic liquids, paints, food products, solution viscosities of polymers, etc.

DETAILED DESCRIPTION OF THE INVENTION

Figure 1:
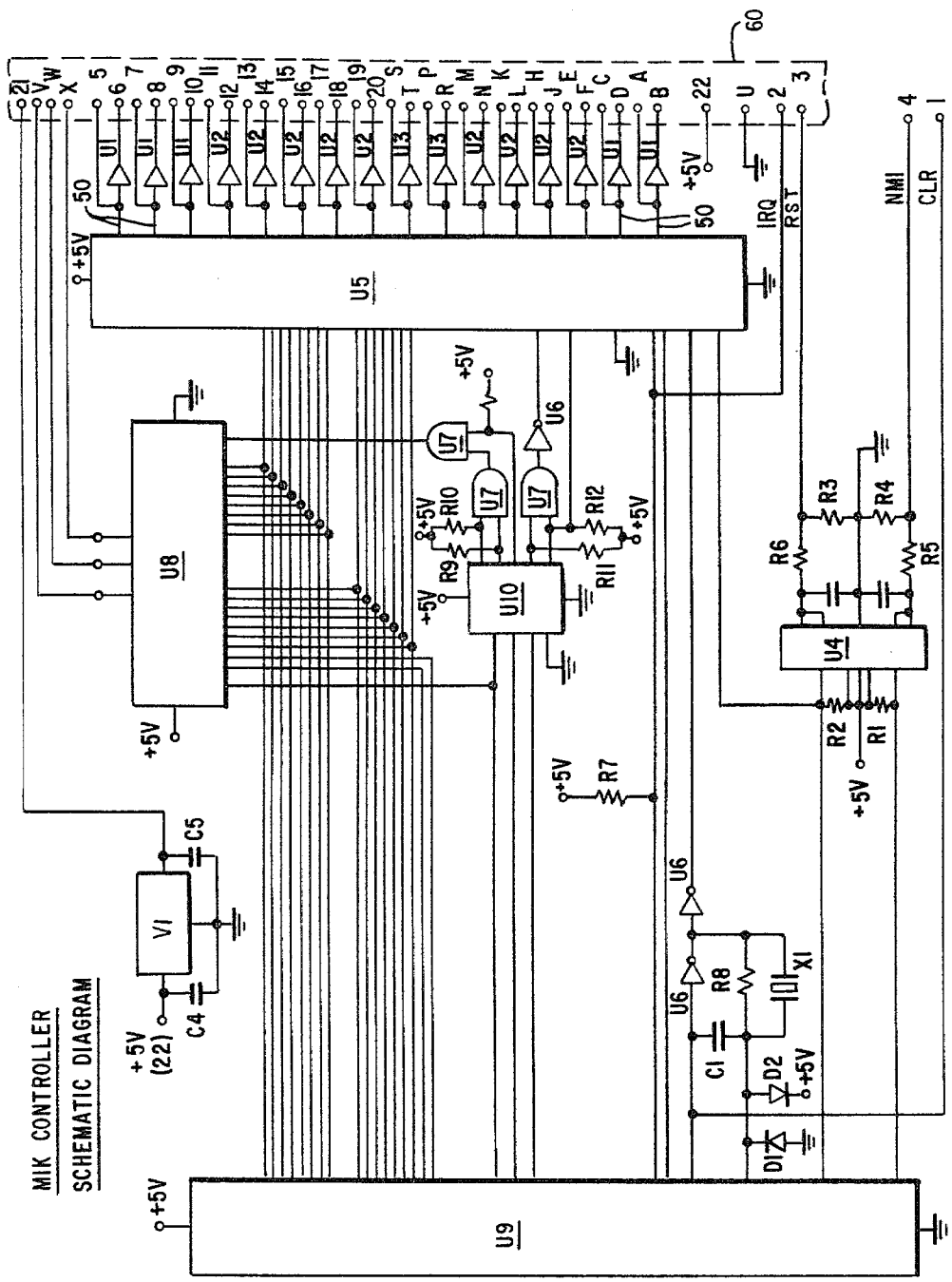
FIG. 1 is a schematic diagram of the microprocessor controller and associated circuitry in accord with the present invention.

Referring more specifically to the drawings, FIG. 1 shows a schematic diagram of the preferred embodiment of the present invention. The unit shown uses a QIX, Inc. microcomputer which uses the MIK 6503 microprocessor controller, U9.

MIK is a single card microcomputer specifically designed for controller applications. Completed programs can be stored in either an on-board EPROM or PROM U8 for execution by MIK, providing a nonvolatile program store for controller applications. MIK has 16 input/output (I/O) lines, 50, which may be programmed as input or output ports. For output, on-board open collector drivers, U1, U2, U3, will sink up to 40 ma allowing direct driving of relays, power transistors, or LEDs from the MIK board without additional external circuitry.

MIK pinouts permit use of type 2704 or type 2708 erasable programmable read only memories (EPROM) for up to 1K bytes of program storage. Pin compatible programmable read only memories (PROM) may also be used with appropriate external connections on the board edge connector, 60.

The MIK microprocessor controller, U9, includes 128 bytes of random access memory (RAM) for use as scratch pad memory and storage of program variables. MIK also includes a programmable clock capability external to the 6503 microprocessor permitting timed interrupts of the 6503. In addition, MIK has an on-board +5 volt regulator, V1.

FIG. 1 is a schematic diagram of the MIK microprocessor controller board. MIK uses the 6503 microprocessor, U9, together with the 6532 memory, I.O, and timer array, U5, and necessary support circuitry. The on-board crystal controller oscillator, X1, provides an accurate source of timing. Debounce circuitry for the reset and nonmaskable interrupt (NMI) lines is also provided (U4 and its associated resistor/capacitor network).

As can be seen from FIG. 1, both buffered and unbuffered pinouts of the sixteen 6532 I/O lines 50 are provided to the MIK edge connector 60 permitting these lines to be used as inputs, or buffered or unbuffered outputs. Table 1 lists the various components and associated descriptions for the MIK board.

TABLE 1

| COMPONENTS OF CONTROLLER BOARD | | | | | |
|---|---|---|---|---|---|
| COMPONENT | | DESCRIPTION | COMPONENT | | DESCRIPTION |
| U1 | 7407 | Hex Buffer/ Driver (14 pins) | R6 | 1K | +10% ¼w resistor |
| U2 | 7407 | Hex Buffer/ Driver (14 pins) | R7 | 3.3K | +10% ¼w resistor |
| U3 | 7407 | Hex Buffer/ Driver (14 pins) | R8 | 330K | + 5% ¼w resistor |
| U4 | 556 | Dual Timer (14 pins) | R9 | 560 | +10% ¼w resistor |
| U5 | 6532 | Multifunction Support Chip (40 pins) | R10 | 560 | +10% ¼w resistor |
| U6 | 7404 | Hex Inverter Buffer Driver (14 pins) | R11 | 560 | +10% ¼w resistor |
| | | | R12 | 560 | +10% ¼w resistor |
| U7 | 7408 | Quad 2-Input AND Gates (14 pins) | R13 | 560 | +10% ¼w resistor |
| U8 | PROM (or EPROM) | (24 pins) | C1 | 0.22f | +10% 12wv capacitor |
| U9 | 6503 | Microprocessor (28 pins) | C2 | 0.22f | +10% 12wv capacitor |
| U10 | 74145 | BCD to Decimal Decoder (16 pins) | C3 | 10pf | +5% capacitor |
| V1 | 7805 | 3-Term Positive Voltage Regulator | C4 | 1f | Tantulum capacitor |
| R1 | 3.3K | +10% ¼w resistor | C5 | 1f | Tantulum capacitor |
| R2 | 3.3K | +10% ¼w resistor | D1 | IN914 | Diode |
| R3 | 47K | +10% ¼w resistor | D2 | IN914 | Diode |
| R4 | 47K | +10% ¼w resistor | X1 | 1MHz | Crystal |
| R5 | 1K | +10% ¼w resistor | | | |

Table 2 lists the MIK edge connector pinouts. A0 through A7 and B0 through B7 are the sixteen 6532 I/O lines 50. A0B through A7B and B0B through B7B are the buffered versions of these lines.

TABLE 2

| MIK EDGE CONNECTOR | | | |
|---|---|---|---|
| Pin No. | Connection | Pin No. | Connection |
| 1 | ClK | A | B7 |
| 2 | IRQ | B | B7B |
| 3 | Reset | C | B6 |
| 4 | NMI | D | B6B |
| 5 | A0 | E | B5 |
| 6 | A0B | F | B5B |
| 7 | A1 | H | B4 |
| 8 | A1B | J | B4B |
| 9 | A2 | K | B3 |
| 10 | A2B | L | B3B |
| 11 | A3 | M | B2 |
| 12 | A3B | N | B2B |
| 13 | A4 | P | B1 |
| 14 | A4B | R | B1B |
| 15 | A5 | S | B0 |
| 16 | A5B | T | B0B |
| 17 | A6 | U | GND |
| 18 | A6B | V | EPROM (U8) pin 18 |
| 19 | A7 | W | EPROM (U8) pin 19 |
| 20 | A7B | X | EPROM (U8) pin 21 |
| 21 | +V | | |
| 22 | +5 | | |

Note that EPROM U8 (or PROM) pins 18, 19 and 21 are also brought out to the edge connector 60 in FIG. 1. EPROM U8 (or PROM) pins 18, 19, and 21 are brought out to the MIK edge connector tabs V, W and X respectively to allow MIK to be used with either EPROM (types 2704 or 2708) or compatible PROMs. For use with type 2704 or 2708 EPROMs, these pinouts are connected as follows:

V (EPROM pin 18): Ground
W (EPROM pin 19): +12 volts
X (EPROM pin 21): −5 volts

The preferred embodiment of FIG. 1 employs a 1K EPROM type 2758 which requires only +5 volt inputs.

A typical PROM requirement (Signetics N82S141 4K PROM; TI SN74S474 4K PROM; TI SN74S478 8K PROM) is as follows:

V (PROM pin 18): +5 volts
W (PROM pin 19): +5 volts
X (PROM pin 21): Ground

The data sheet for the particular PROM selected should be checked for different requirements. The selection of EPROM or PROM components is discretionary with the user and dependent upon the various requirements of a particular application.

IRQ (edge connector pinout 2) is the timer interrupt request line from the on-board programmable timer in the 6532 support chips, U5. This line is connected to the 6503 microprocessor, U9, IRQ input. It is also brought out to the edge connector, 60, for potential timing of external events. The pin is normally high with a low indicating an interrupt from the 6532 chip, U5.

RST (edge connector pinout 3) is the processor reset line. A +5 volt pulse (supplied, for example, through a momentary contact switch) will reset the 6503 processor, U9, and the 6532 support chip, U5. The processor will immediately jump to the location specified in the reset vector and begin code execution.

NMI (edge connector pinout 4) is the nonmaskable interrupt line to the 6503 microprocessor, U9. A +5 volt pulse on this line will cause the processor to jump to the location indicated in the NMI vector. Both the NMI and RST vectors are debounced on the MIK board by dual timer U4.

The MIK board is designed to operate from a single +5 volt supply except for extra voltage requirements of some EPROMs as already described. MIK has an on-board 7805 positive voltage regulator, V1, to supply +5 volts to the board components. The input to this regulator is brought out to edge connector pinout 21. Supplying +V to pin 21 will result in +5 volts being distributed to the board. The +5 volts is also brought out to edge connector pinout 22.

Figure 2:
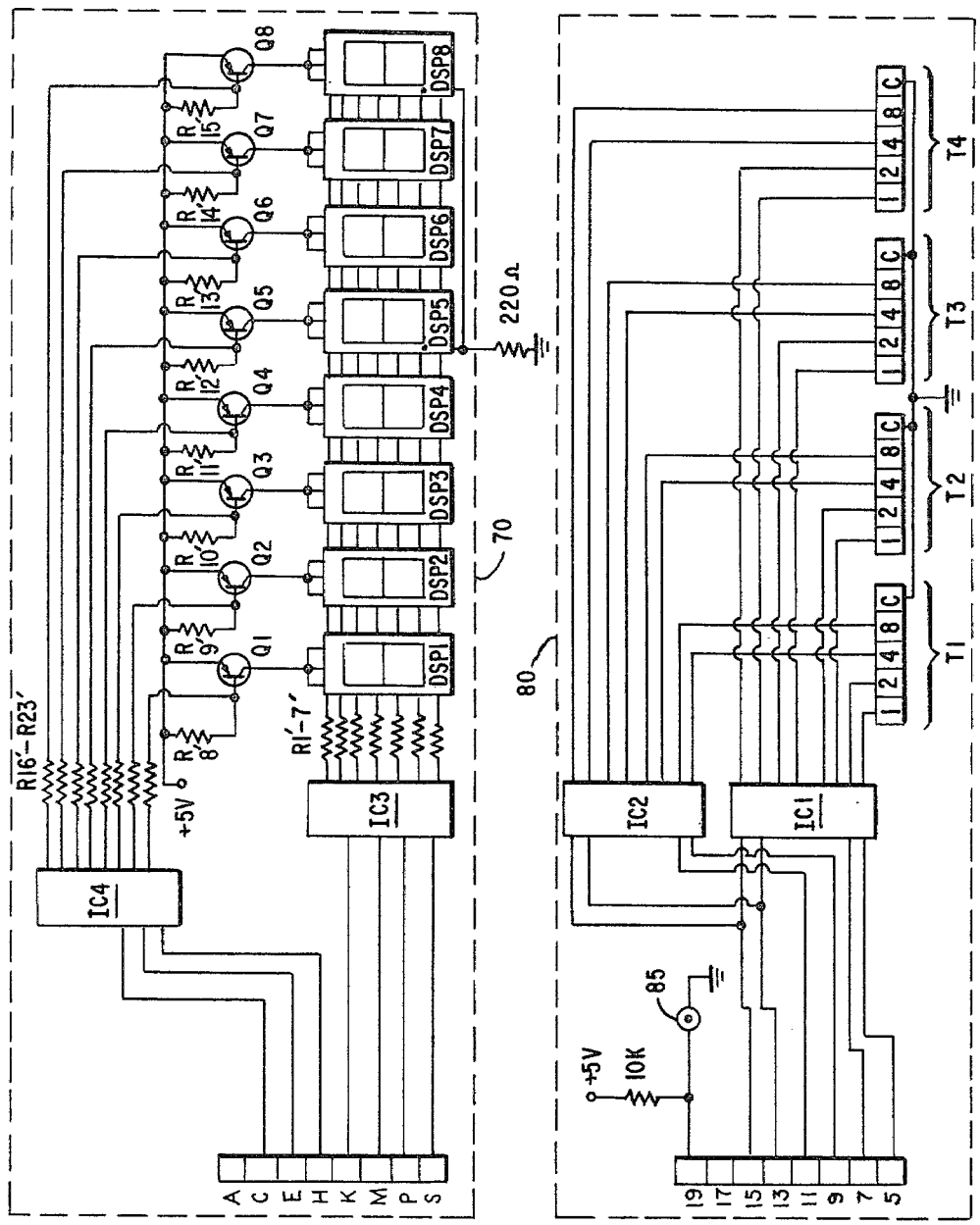
FIG. 2 is a schematic diagram of the peripheral interface adaptor board used in conjunction with the controller board of FIG. 1 in accord with the present invention.
Figure 3:
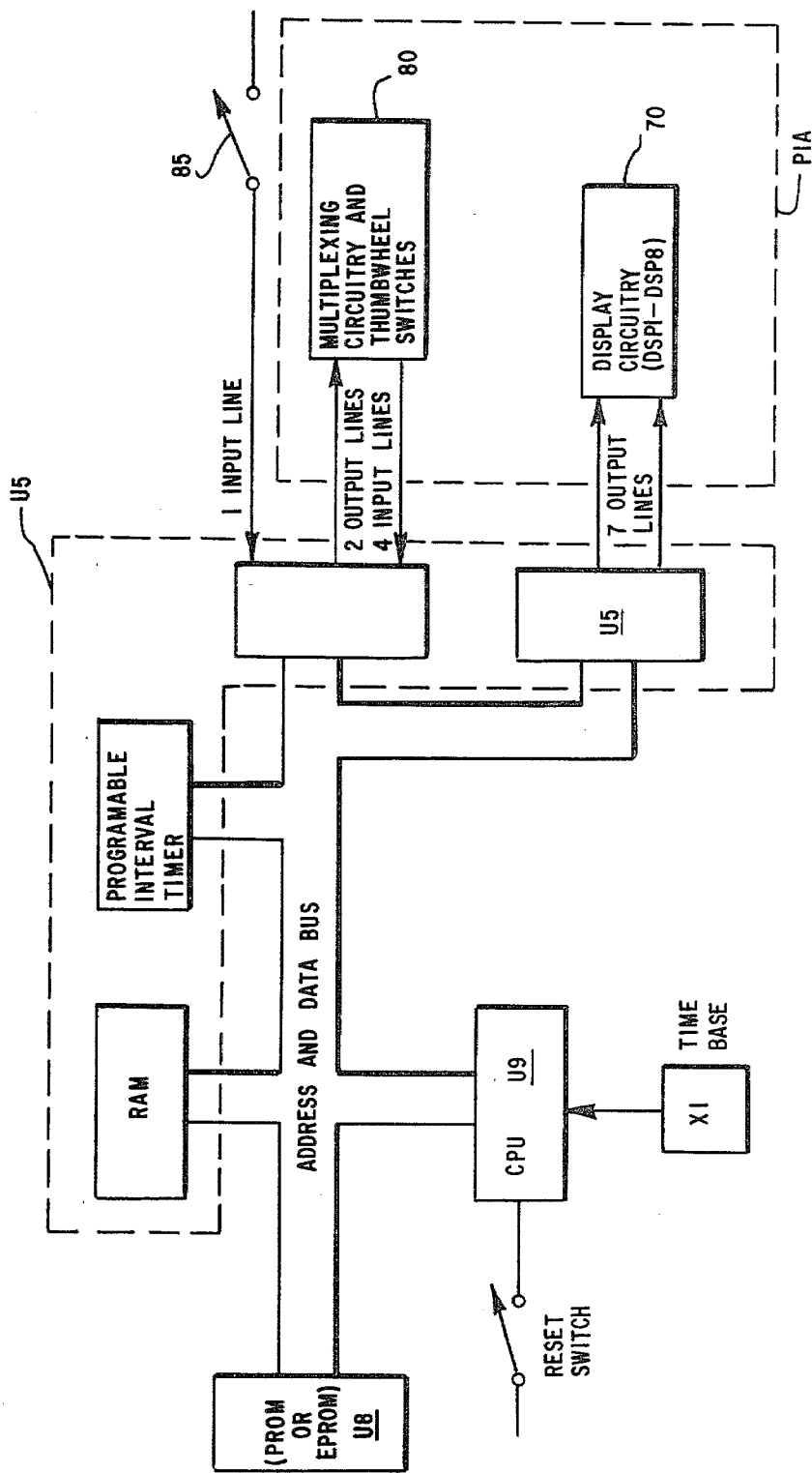
FIG. 3 is a block diagram of the method of operation of the present invention.

A peripheral interface adaptor (PIA) board comprising two parts, display segment 70 and input segment 80, as shown in FIG. 2, is employed to perform the I/O functions of the invention. A block diagram of the MIK controller and PIA board interfaced to comprise the system of the present invention is shown in FIG. 3. The edge connector 60 pinouts of the MIK controller, A, C, E, H, K, M, P and S are connected to PIA board display segment 70, as shown. Similarly, edge connector pinouts 5, 7, 9, 11, 13, 15, 17 and 19 of the MIK controller are connected to the edge connector of PIA board input segment 80.

The numbered pin connectors on the PIA board integrated circuits (IC1–IC4) have been deleted from the ICs in FIG. 2. The particular pin connections that should be made to duplicate the circuit of FIG. 2 will be obvious to those skilled in the art after examining the specifications of the ICs to be used. In particular, IC1 and IC2 of PIA board input segment 80 are both type 74153 integrated circuits with +5 volts on pin 16, and with pins 8, 1, and 15 connected to ground (for simplicity, the ground and +5 volt connections are not shown on FIG. 2). Considering the integrated circuits of PIA board display segment 70, IC3 is type 7447 integrated circuit with +5 volts on pins 16, 3, and 4 and pin 8 grounded; IC4 is type 74145 with +5 volts on pin 16 and pins 8 and 12 grounded. In addition, MIK controller edge connector 60 pinouts 22 and X are connected to +5 volts, pinouts U, V and W are connected to ground, and pinout 3 is connected to a reset switch.

The light emitting diodes (LED) of PIA board display segment 70, denoted DSP1–DSP8 in FIG. 2, are type 707; transistors Q1–Q8 are 2N3906 or equivalent; R1'–R7' are nominally 82 ohm, one-quarter watt resistors; R8–R15 are nominally 220 ohm, one-quarter watt resistors; and R16–R23 are nominally 1000 ohm, one-quarter watt resistors.

PIA board input segment 80 is shown in FIGS. 2 and 3 with thumbwheel switches, T1–T4. The numbered pin connections for each thumbwheel switch are also shown in FIG. 2, with the "common" pin C of each switch connected to ground. Alternative input means will be obvious to those skilled in the art. As there are insufficient inputs to the MIK controller to handle all thumbwheel switch leads simultaneously, T1–T4 are each connected to a multiplex chip (IC1 or IC2) so that each switch's status can be read individually by the MIK controller through edge connector 60.

While the MIK controller board of FIG. 1 has an on-board +5 v regulated power supply V1, an external regulated supply may be used if a higher rated supply is desired. In this event, the on-board supply V1 must be disabled or bypassed on edge connector 60. A Model EMA-5/6A regulated power supply manufactured by Power/Mate Corporation of Hackensack, N.J., is one example of such an external supply. Other comparable units can also be used—the main requirement is that the source provide regulated +5 volts direct current and be capable of delivering about 1.0 to 1.5 amps.

The components and circuitry described thus far correspond to the preferred embodiment currently in use. It will be obvious to those skilled in the art that substitutions of alternative equivalent components can be made without departing from the spirit of the invention.

Specifically, alternative EPROM components include Motorola's type 6834 and 2704, Natural Semiconductor's type 2708, and Intel's type 8708. PROM components that can also be used in accord with the method of this invention include Signetics' type N82S141, and Texas Instruments' type SN74S474 and SN74S478; while compatible ROMs include Intel's type 8308 and National Semiconductor's type DM77596. In addition, the 6532 microprocessor and EPROM chips can be replaced, for example, by a single 6530 chip made by Rockwell or MOS. Intel's 8085 microprocessor and 8155 RAM, I/O, Timer can be used in place of the 6503 and 6532 package. In general, those skilled in the art will recognize that numerous 4 bit, 8 bit or 16 bit processors can be used in conjunction with the method of the present invention.

With reference to the integrated circuits (IC1–IC4) of the PIA board, the 7400 series preferred is an industry standard produced by a large number of domestic and foreign manufacturers, including National Semiconductor Corp., Texas Instruments and Signetics. Low power consumption CMOS and Schottky-type TTL devices of equivalent function may also be used. The type 2N3906 transistors (Q1–Q8) used on the PIA board in display segment 70 is used in a switching mode. Such transistors can be replaced by well known low power, general purpose PNP transistor of equivalent or superior characteristics, with a power dissipation of about 300 milliwatts, including, for example, type 2N2222. The I/O display means (DSP1–DSP8) employed in the preferred embodiment, Data-Lit 707, may be replaced by any seven segment display LED (common anode) with similar electrical characteristics. The selection of alternates should be obvious to those skilled in the art and would include the MAN 72, MAN 4710, and FND 507.

In the operation of the preferred method and device of this invention, the timer actuating switch 85 on the extrusion plastometer is normally in a closed position before the start of a measurement. After the thermoplastic material is loaded into the extrusion plastometer, the operator presses the reset switch which clears both a result display and a timer display. The I/O ports 50 are initialized by the program and the program then starts the timer display counting by tenths of a minute to time the preheat period for the material. During this period, the program periodically checks the status of the actuating switch 85 and continues to display the preheat time until switch 85 opens. At the end of the desired preheat time, the operator simply applies the required load to the piston of the plastometer. As the piston displaces the material in the plastometer, the actuating switch 85 is opened, signalling the start of the measurement period. When switch 85 opens, the program extinguishes both displays to indicate a test is in progress.

A "debounce" routine is included in the program to ignore very short-term ($\leq \frac{1}{2}$ sec.) contact bounce in switch 85. If the program detects re-closure of switch 85 in less than $\frac{1}{2}$ sec., a false start has occurred and the program loops back to reinitialize all counters, restart and display the preheat timer, and again await a true switch 85 signal. If switch 85 remains open for greater than $\frac{1}{2}$ second, the switch status is then periodically checked by the program through an interrupt routine which checks the status of the switch at 10 millisecond intervals. The time base is derived from a 1 MHz crystal controlled source X1. Upon re-closure of the actuating switch 85, signalling the displacement of the appropriate volume of material, the thumbwheel switches are read to input the numerical factor F for the particular material into the program. The program performs the necessary calculation of the flow rate by a BCD division algorithm and then displays the result. The result continues to be displayed until the reset switch is again pressed. As noted in FIG. 2, a permanent decimal point is provided between the fourth and fifth digits (DSP4–DSP5) of the result display and between the two digits (DSP7–DSP8) of the timer display. The LED forming the decimal point and a current limiting resistor R24 are connected between +5 volts d.c. and ground.

We claim:

1. In a device for determining the flow rate of a thermoplastic material in accord with Procedure B of ASTM Method D1238 using an extrusion plastometer, the improvement comprising
    means for entering one or more numerical factors specified by said ASTM Method D1238 for said thermoplastic material into an input/output device capable of being read by a microprocessor,
    means for initiating an electronically timed interval when a change of state is detected in a switch designed to undergo a first change of state after displacement of said thermoplastic material begins in said plastometer,
    means for checking the status of said switch at predetermined intervals,
    means for ending said electronically timed interval when said switch undergoes a second change of state upon the displacement of a predetermined volume of said thermoplastic material,
    means for determining the duration of said timed interval,
    means for calculating the flow rate for said thermoplastic material by dividing said factor by the duration of said timed interval, and
    means for displaying said flow rate in a convenient input/output device.

2. The device of claim 1 wherein said means for entering said numerical factors is a set of thumbwheel switches.

3. The device of claim 1 wherein said means for displaying said flow rate is a set of LED displays.

4. The device of claim 3 wherein said means for entering said numerical factors is a set of thumbwheel switches.

5. The device of claim 1 wherein said means for entering said numerical factors is a keyboard.

6. The device of claim 1 wherein said means for displaying said flow-rate is a printer.

7. The device of claim 1 wherein a preheat timer is initiated prior to the start of the extrusion of said thermoplastic material.

* * * * *

UNITED STATES PATENT OFFICE
CERTIFICATE OF CORRECTION

Patent No. 4,333,336      Dated June 8, 1982

Inventor(s) Carl A. Myerholtz and Ralph W. Myerholtz, Jr.

It is certified that error appears in the above-identified patent and that said Letters Patent are hereby corrected as shown below:

| Patent Col. | Line | |
|---|---|---|
| 3 | 14 | "again, (closes)," should read --again (closes),-- |
| 3 | 38 | "(BDC)" should read --(BCD)-- |
| 5 | 49 | "I.0," should read --I/O,-- |
| 8 | 16 | "R8 - R15" should read --R8' - R15'-- |
| 8 | 17 | "R16 - R23" should read --R16' - R23'-- |
| 8 | 48 | "Natural" should read --National-- |

Signed and Sealed this

Fourteenth Day of June 1983

[SEAL]

Attest:

DONALD J. QUIGG

Attesting Officer     Acting Commissioner of Patents and Trademarks